(12) United States Patent
Niwa et al.

(10) Patent No.: US 6,348,333 B1
(45) Date of Patent: Feb. 19, 2002

(54) VEGF-BINDING KDR POLYPEPTIDE

(75) Inventors: Mikio Niwa; Masaji Okamoto; Tomoe Matsumoto; Toshiaki Segawa, all of Ibaraki (JP)

(73) Assignee: Toa Gosei Co., Ltd., Tokyo (JP)

( * ) Notice: Subject to any disclaimer, the term of this patent is extended or adjusted under 35 U.S.C. 154(b) by 0 days.

(21) Appl. No.: 09/142,956

(22) PCT Filed: Jan. 16, 1998

(86) PCT No.: PCT/JP98/00140

§ 371 Date: Mar. 4, 1999

§ 102(e) Date: Mar. 4, 1999

(87) PCT Pub. No.: WO98/31794

PCT Pub. Date: Jul. 23, 1998

(30) Foreign Application Priority Data

Jan. 17, 1997 (JP) .............................................. 9-019706

(51) Int. Cl.[7] ........................ C07K 14/71; C07K 19/00; C12N 5/10; C12N 15/10
(52) U.S. Cl. .................... 435/69.4; 536/23.1; 536/23.5; 536/23.4; 530/350; 435/69.1; 435/320.1; 435/325; 435/252.3; 435/254.11
(58) Field of Search ................................ 530/300, 350, 530/387.1; 536/23.1, 23.5, 23.4; 435/320.1, 69.1, 325, 252.3, 254.11, 69.4

(56) References Cited

U.S. PATENT DOCUMENTS 5,952,199 A * 9/1999 Davis-Smith

FOREIGN PATENT DOCUMENTS

| WO | WO 94/10202 | 5/1994 |
| WO | WO 94/21679 | 9/1994 |
| WO | WO 95/33050 | 12/1995 |

OTHER PUBLICATIONS

Plowman et al., Receptor tyrosine kinases as targets for drug intervention, DN&P 7(6):334–339, Aug. 1994.*

Davis-Smyth et al., The second immunoglobulin–like domain of the VEGF tyrosine kinase receptor Flt-1 determines ligand binding and may initiate a signal transduction cascade, EMBO J., 15(18): 4919–27, Sep. 1996.*

Aiello et al., "Suppression of retinal neovascularization in vivo by inhibition of vascular endothelial growth factor (VEGF) using soluble VEGF–receptor chimeric proteins" Proc Natl. Acad. Sci. 92:10457–10461 (1995).

Boocock, et al., "Expression of Vascular Endothelial Growth Factor and Its Receptors flt and KDR in Ovarian Carcinoma" Journal of the National Cancer Institute, 87:506–516 1995.

Brown et al., "Expressions of Vascular Permeability Factor (Vascular Endothelial Growth Factor) and Its Receptors in Adenocarcinomas of the Gastrointestinal Tract[1]" Cancer Research 53:4727–4735 (1993).

Capon et al., "Designing CD4 immunoadhesins for AIDS therapy" Nature 337:525–531 (1989).

Dvorak et al., "Distribution of Vascular Permeability Factor (Vascular Endothelial Growth Factor) in Tumors: Concentration in Tumor Blood Vessels" J. Exp. Med. 174:1275–1278 (1991).

Flores et al., "Angiogenesis: an update" Histol Histopath 9:807–843 (1994).

Folkman "What is the Evidence that Tumors Are Angiogenesis Dependent?" Journal of the National Cancer Institute, 82:4–6 (1990).

Gengrinovitch et al., "Platelet Factor–4 Inhibits the Mitogenic Activity of $VEGF_{121}$ and $VEGF_{165}$ Using Several Concurrent Mechanisms" The Journal of Biological Chemistry, 270:15059–15065 (1995).

Kendall et al., "Inhibition of vascular endothelial cell growth factor activity by an endogenously encoded soluble receptor" Proc. Natl. Acad. Sci. 90:10705–10709 (1993).

Kendall et al., "Specificity of Vascular Endothelial Cell Growth Factor Receptor Ligand Binding Domains" Biochemical & Biophysical Research Communications, 201:326–330 (1994).

Kim et al., "Inhibition of vascular endothelial growth factor–induced angiogenesis suppresses tumor growth in vivo" Nature, 362:841–844 (1993).

King et al., "Expression, purification and characterization of a mouse–human chimeric antibody and chimeric Fab' fragment" Biochem Journal, 281:317–323 (1992).

Kondo et al., "Signigicance of Vascular Endothelial Growth Factor/Vascular Permeability Factor for Solid Tumor Growth, and Its Inhibition by the Antibody" Biochemical & Biophysical Res. Com. 194:1234–1241 (1993).

Lane et al., Radioimmunotherapy of metastatic colorectal tumours with iodine–131–labelled antibody to carcinoembryonic antigen: phase I/II study with comparative biodistribution of intact and f(ab+e,acu +ee $)_2$ antibodies British Journal of Cancer, 70:521–525 1994.

* cited by examiner

Primary Examiner—Claire M. Kaufman
(74) Attorney, Agent, or Firm—Fish & Richardson P.C.

(57) ABSTRACT

A novel polypeptide is provided, which can be utilized to treat diseases accompanying neovascularization, such as solid tumors, and is useful as a low molecular weight VEGF inhibitor. The polypeptide contains immunoglobulin-like domain 1 and immunoglobulin-like domain 2 of the extracellular domain of the VEGF receptor KDR. Since it has smaller molecular weight than the conventional polypeptides with retaining VEGF inhibitory activity, it is expected that it can be readily expressed using recombinant DNA techniques and infiltrates into diseased sites more quickly.

16 Claims, 5 Drawing Sheets

VEGF-BINDING KDR POLYPEPTIDE

This is the National Stage of International Patent Application No. PCT/JP98/00140, with an international filing date of Jan. 16, 1998, now pending.

TECHNICAL FIELD

The present invention relates to polypeptides which are useful as neovascularization inhibitors, and a method of producing them.

BACKGROUND ART

It is known that pathological neovascularization can be a symptom or the cause of certain diseases. An example of pathological neovascularization is the occurrence of a solid tumor. For the growth of tumor tissue beyond the diameter of 1 to 2 mm, newly formed blood vessels need to extend from the existing blood vessels to reach the tumor tissue. When the blood vessel reaches the tumor tissue, its growth is explosively accelerated (J. Folkman, J. Natl. Cancer Inst., 82:4 (1990)). On the other hand, diabetic retinopathy is accompanied with pathological neovascularization of the retina, which may lead to the loss of eyesight. Moreover, pathological neovascularization is also seen in such diseases as chronic rheumatoid arthritis, psoriasis, hemangioma, scleroderma, and neovascular glaucomas, and it is considered to be one of the main symptoms (J. Folkman and N. Engle, J. Med., 320:1211 (1989)). Therefore, it may be possible to use substances that inhibit neovascularization for the treatment of tumors and other diseases mentioned above.

Vascular endothelial cells are the cells that constitute the innermost layer of the blood vessel. Neovascularization occurs when vascular endothelial cells proliferate upon stimulation by growth factors, physiologically active substances, or mechanical damages.

Known growth factors that can directly or indirectly stimulate the proliferation of vascular endothelial cells include basic fibroblast growth factor (bFGF), acidic fibroblast growth factor (aFGF), vascular endothelial cell growth factor (VEGF), platelet-derived endothelial cell growth factor (PD-ECGF), tumor necrosis factor-$\alpha$ (TNF-$\alpha$), platelet-derived growth factor (PDGF), epidermal growth factor (EGF), transforming growth factor-$\alpha$ (TGF-$\alpha$), and hepatocyte growth factor (HGF) (L. Diaz-Flores et al., Histol. Histopath., 9:807 (1994)). Among these factors, vascular endothelial cell growth factor (VEGF) can be distinguished from the other growth factors by the fact that its action is very specific to vascular endothelial cells. In other words, the VEGF receptor is found in very few cells other than vascular endothelial cells.

VEGF is a glycoprotein whose molecular weight is 40,000–45,000, and exists as a dimer (P. W. Leung et al., Science, 246:1306 (1989), P. J. Keck et al., Science, 246:1319 (1989)). VEGF acts, by binding to the VEGF receptor, to promote cell proliferation and enhance membrane permeability.

The following reports suggest the involvement of VEGF in tumor growth.

Many tumor cells secrete VEGF (S. Kondo et al., Biochem. Biophys. Res. Commun., 194:1234 (1993)). When tumor tissue sections are stained with an anti-VEGF antibody, the tumor tissue is strongly stained as well as the newly formed blood vessels surrounding it (H. F. Dvorak et al., J. Exp. Med. 174:1275 (1991), L. F. Brown et al., Cancer Res., 53:4727 (1993)). Growth of a transplanted tumor is suppressed in the mouse in which one of the VEGF receptors is genetically inactivated (B. Millauer et al., Nature, 367:576 (1994)). Anti-VEGF neutralizing antibodies exhibit antitumor activities in the tumor-bearing mice (K. J. Kim et al., Nature, 362:841 (1993), S. Kondo et al., Biochem. Biophys. Res. Commun., 194:1234 (1993)).

From these facts, it is considered that VEGF secreted by tumor cells play a major role in neoplastic neovascularization.

In humans there are two known VEGF receptors, FLT (M. Shibuya et al., Oncogene, 5:519 (1990), C. DeVries et al., Science, 255:989 (1992)) and KDR (B. I. Terman et al., Biochem. Biophys. Res. Commun., 187:1579 (1992)). The extracellular domain of FLT and KDR has the structure constituted by seven immunoglobulin-like domains as shown in FIG. 1. The cDNA or the soluble-type receptor of FLT has been cloned (R. L. Kendal and K. A. Thomas, Proc. Natl. Acad. Sci. U.S.A., 90:10705 (1993)). The polypeptide encoded by this cDNA corresponds to the first through to the sixth immunoglobulin-like domains of the FLT extracellular domain. This polypeptide inhibited VEGF activity by binding to VEGF with an affinity comparable to that of the full-length FLT. Regarding KDR, it is also known that the genetically engineered first through sixth immunoglobulin-like domains of the extracellular domain bind to VEGF (R. L. Kendal et al., Biochem. Biophys. Res. Commun., 201:326 (1994)).

As described above, since the mouse anti-VEGF neutralizing antibodies exhibit antitumor activity, they are expected to be useful as anti-cancer agents. However, when a mouse antibody is administered to humans, human antibodies against the mouse antibody may be produced, which could lead to neutralization of the mouse antibody or might cause anaphylactic shock. In order to avoid these undesirable effects, it is necessary to modify the amino acid sequence of the mouse antibody to be closer to that of the human antibody through chimerization (S. L. Morrison et al., Proc. Natl. Acad. Sci. U.S.A., 81:6851 (1989)) or humanization without reducing the neutralizing activity of the mouse antibody. Since this method requires advanced techniques and knowledge, experience, and labor, the results depend on individual cases and are not always successful and 100%-humanized antibodies cannot be obtained by these methods. Another method utilizes the transgenic mice that produce human antibodies for immunization (S. Wagner et al., Nucleic Acid Res., 22:1389 (1994)), but here again highly specialized techniques are required.

As described above, since the extracellular domain of the VEGF receptor specifically binds to VEGF with high affinity, thereby inhibiting the VEGF activity, it can be considered useful as an inhibitor against neovascularization. Moreover, the possibility of antibody production in a human recipient is expected to be low because it is a polypeptide of human origin. On the other hand, when a polypeptide that does not naturally exist much in the human body is administered, it is metabolized very rapidly. For example, the plasma half-life of soluble CD4, which is a receptor for HIV, is 15 minutes (D. J. Capon et al., Nature, 337:525 (1989)), and that of interferon $\gamma$ is 30 minutes (I. Rutenfranz and H. Kirchner, J. Interferon Res., 8:573 (1988)).

As a method for prolonging the plasma half-life, it is known to utilize a fusion polypeptide genetically engineered by combining the polypeptide of interest with a molecule having a long plasma half-life, such as an antibody molecule.

In the case of CD4, the plasma half-life was increased from 15 min to 48 hr when it was chimerized with the Fc domain of IgG1 (D. J. Capon et al., Nature, 337:525 (1989)). Such a fusion polypeptide with the Fc domain of an antibody is also expected to provide an effect to induce the effector functions that the antibody possesses, i.e., complement-dependent cytotoxicity (D. B. Amos et al., Transplantation, 7:220 (1969)) and antibody-dependent cytotoxicity (A. Y. Liu et al., Proc. Natl. Acad. Sci. U.S.A., 84:3439 (1987)). Furthermore, it is expected to drastically improve the apparent affinity when the fusion polypeptide binds to a ligand on a solid phase, such as the surface of a membrane or the extracellular matrix, since the dimerization via the Fc domain enable each molecule to bind to the ligand at two sites.

When a fusion polypeptide constructed with an antibody is utilized, it is desirable to select a polypeptide with a low molecular weight as a starting material because the molecular weight increases through the fusion. This is because, if a high molecular weight polypeptide is used, the molecular weight of the corresponding DNA is also high, which is to be handled by gene manipulation upon production of the recombinant host that produces the fusion polypeptide. In general, the larger the molecular weight of the DNA to be introduced, the less efficient the transfection of the host becomes, thereby reducing the productivity of the recombinant host. Also in general, the larger the molecular weight of the recombinant polypeptide to be produced, the smaller the amount of product tends to be. Moreover, for the treatment of solid tumors, large molecular weight polypeptides are disadvantageous as these polypeptides poorly infiltrate the diseased area (D. M. Lane et al., Br. J. Cancer, 70:521 (1994)).

DESCLOSURE OF THE INVENTION

The present inventors have made earnest efforts in discovering small molecular weight polypeptides among those that can inhibit neovascularization by specifically inhibiting VEGF, and particularly those which are contained in the extracellular domain of the VEGF receptor. As a result, it has been found that polypeptides containing immunoglobulin-like domain 1 and immunoglobulin-like domain 2 of the extracellular domain of KDR can inhibit the VEGF activity by specifically binding to VEGF with high affinity, thereby completing the present invention. The term "polypeptides" used herein means polypeptides constituted by amino acids that are covalently bound to each other via peptide bonds, and their lengths are not limited.

Though the polypeptide consisting of immunoglobulin-like domain 1 and immunoglobulin-like domain 2 of the extracellular domain of KDR is preferably used in the present invention because of its low molecular weight, those that contain other domains can also be used. For example, the polypeptides include the polypeptides containing immunoglobulin-like domains 1 through 3, those containing immunoglobulin-like domains 1 through 4, and those containing immunoglobulin-like domains 1 through 5. The polypeptides of the invention also include those containing immunoglobulin-like domains 1 through 5 that are deficient in any one or two domains within immunoglobulin domains 3 through 5. The amino acid sequence of the polypeptides of the present invention may be modified partially by substitution or the like as long as the polypeptides can inhibit the VEGF activity by binding to VEGF. One skilled in the art could readily perform such modification of the amino acids by known methods. As a matter of course, the polypeptides such as those containing immunoglobulin-like domains 1 through 6 and those containing immunoglobulin-like domains 1 through 7 can bind to VEGF specifically with high affinity. However, their molecular weights are too high to achieve the object of the present invention that "the polypeptide is easily expressed by recombinant DNA techniques and rapidly infiltrates into the diseased area." Although the borders between adjacent domains of KDR are not clearly determined, each domain is defined herein as the one that contains the amino acid sequence designated by the following amino acid residue numbers within the entire amino acid sequence of KDR represented by SEQ ID NO: 14, which has been already published. The amino acid residue numbers are the same as those shown in SEQ ID NO: 14. Namely, they correspond to the residue numbers counted from the amino-terminal "Ala" of the mature KDR, which is position 1 in the SEQ ID NO: 14.

Immunoglobulin-like domain 1: 1–115
immunoglobulin-like domain 2: 116–214
Immunoglobulin-like domain 3: 218–319
Immunoglobulin-like domain 4: 319–392
Immunoglobulin-like domain 5: 393–533
Immunoglobulin-like domain 6: 534–645
Immunoglobulin-like domain 7: 646–750

Furthermore, the present invention includes the polypeptides constructed by fusing the above extracellular domain of KDR with another protein (such as the Fc domain of immunoglobulins).

These peptides can be produced by the following procedures. A total RNA is extracted by the acid phenol method (P. Chomzynski and N. Sacchi, Anal. Biochem., 162:156 (1987)) from the cultured human vascular endothelial cells, such as human umbilical chord-derived vascular endothelial cells (commercially available from Iwaki Glass, Morinaga Dairy Products, or Kurabo), and purified into a poly $A^+$ RNA using an oligo dT cellulose. A single-stranded or double-stranded cDNA is synthesized using this RNA as a template, reverse transcriptase, and the oligo dT (12–16) primer. The poly $A^+$ RNA and the cDNA can be prepared in accordance with J. Sambrook et al., "Molecular Cloning" (Cold Spring Harbor Laboratory Press, 1989). Alternatively, the commercially available poly $A^+$ RNA preparation reagents (oligotex-dT30, Takara) or cDNA synthesis kit (Pharmacia Biosystem) can be used. If a KDR CDNA has been already cloned from a cDNA library, the DNA corresponding to the region to be expressed can be isolated by digestion with appropriate restriction enzymes and introduced directly into an expression vector.

Next, a desired part of the DNA can be amplified by PCR using the cDNA obtained above as the template (Michael A. Innis et al., "PCR protocols", Academic Press Inc., 1990). For instance, the following primers may be used. The primer DNA can be synthesized with a DNA synthesizer (Applied Biosystems, Japan Millipore Ltd., etc.) or custom-made (Sawadee Technology). For example, in the case of obtaining a cDNA encoding immunoglobulin-like domains 1 through 6, the following primers can be used:

upstream primer:

5' N(3–5) X(6) ATGGAGAGCAAGGTGCTGCTG (SEQ ID NO: 2)

downstream primer:

5' N(3–5) Y(6) ACGCTCTAGGACTGTGAGCTG (SEQ ID NO: 3).

In the case of obtaining a CDNA encoding immunoglobulin-like domains 1 through 3, the following primers can be used:

upstream primer:

5' N(3–5) X(6) ATGGAGAGCAAGGTGCTGCTG (SEQ ID NO: 2)

downstream primer:

5' N(3–5) Y(6) AGATTCCATGCCACTTCCAAA (SEQ ID NO: 4).

In the above sequences, N stands for A, C, G, or T; X or Y stands for a restriction enzyme recognition sequence; and the numeral in the parentheses indicates the number of nucleotides. Specifically, N(3–5) means that there are 3 to 5 nucleotides of A, C, G, and T, and X(6) or Y(6) indicates the recognition site for a 6-base cutter restriction enzyme. It is desirable to choose sequences that are found in neither the DNA fragment to be amplified nor the vector to which the fragment will be inserted as the restriction enzyme recognition sequences in the above. Referring to the nucleotide sequence shown in SEQ ID NO: 1, the downstream primers can be appropriately designed to amplify the DNA fragments encoding the desired carboxy-termini. When inserted into an expression vector, it should be noted that the polypeptide-coding sequences must be placed under the control of the promoter sequence. Parts of the primer sequences which correspond to the flt DNA sequence do not need to be exactly limited to 21 bases, but could be about 17–25 bases. Although the condition for PCR can be a standard one as described in the "PCR Protocols" above, the reaction may be optimized to achieve a better efficiency by appropriately changing various parameters (e.g., $Mg^{2+}$ concentration, annealing temperature, extension time, the number of cycles, etc.), since the reaction proceeds differently depending on the template quantity and the primer sequences. As the DNA polymerase used for PCR, Pfu polymerase (Stratagene), which possesses a proofreading (3' exonuclease) activity, or Taq polymerase supplemented with Pfu polymerase will provide a better fidelity during the PCR amplification than Taq polymerase alone (W. M. Barnes, Proc. Natl. Acad. Sci. U.S.A., 91:2216 (1994)).

Because the sequence of the DNA fragment to be amplified by PCR is known in this case, whether the desired DNA fragment has been obtained can be determined by, after amplification, confirming its size by agarose gel electrophoresis, recovering the fragment from the gel, digesting it with appropriate restriction enzymes, and examining the resulting electrophoresis pattern. Agarose gel electrophoresis, recovering of DNA fragments from the gel, and restriction enzyme digestions can be done according to the "Molecular Cloning" above. A commercial kit which utilizes glass beads (for example, BIORAD Prep-A-Gene) can be used for recovering DNA from a gel.

The recovered DNA fragment is digested with the restriction enzymes capable of cutting X(6) and Y(6) on both ends, deproteinated by the phenol treatment, ethanol-precipitated, and resuspended in an appropriate buffer, such as TE (10 mM Tris-HCl (pH 7.5)/1 mM EDTA). Similarly, the cloning sites of an appropriate expression vector are digested with the restriction enzymes capable of cleaving X(6) and Y(6), agarose gel electrophoresis is performed, and the vector DNA is recovered. Through this procedure, a small fragment between the X(6) and Y(6) recognition sites is eliminated. The DNA fragment to be inserted and the digested vector DNA are mixed at a ratio of, for example, vector DNA:DNA insert=1:5 to 1:10, and ligated using T4 DNA ligase. The ligation product is then added to competent E. coli cells, the transformation of the cells is performed, and transformants are screened by the antibiotic resistance on a culture medium containing the antibiotic corresponding to the selection marker (e.g., ampicillin resistance, kanamycin resistance, etc.) encoded by the vector.

The recombinant expression vector, to which the DNA fragment has been inserted, can be selected by examining the restriction enzyme digestion patterns of the plasmids in the antibiotic-resistant transformants. Alternatively, whether a transformant is a recombinant or not can be examined by performing a PCR reaction on the whole bacteria as the template, using the same set of primers as used to amplify the insert DNA, and detecting the presence or absence of the amplified target fragment. These series of procedures to obtain recombinant E. coli can be performed according to the "Molecular Cloning" above.

A variety of hosts can be used in order to produce the polypeptides of the present invention. For example, Gram negative and Gram positive bacteria such as Escherichia coli, bacteria belonging to the genus Pseudomonas, Bacillus subtilis, Bacillus brevis, Bacillus liqueniformis, and Bacillus thuringenesis; yeast such as Pichia pastoris, Schizosaccharomyces pombe, and Saccharomyces cerevisiae; Eumycetes such as belonging to the genus Aspergillus; insect cells such as Sf9 (derived from Spodoptera frugiperda), Sf21, TN5 (derived from Trichoplusia ni), and BN4 (derived from Bombyx mori); and mammalian cells such as CHO (derived from the Chinese hamster ovary) and COS (derived from the monkey kidney). The vector can be selected based on the suitability to the host cells. The final transformants may be easily obtained by producing the recombinant DNA first in E. coli using a shuttle vector functioning in the host to be used for production of the polypeptide of the present invention and E. coli. The transformations method used for obtaining the recombinant host that produces the polypeptide of the present invention include the competent cell method for E. coli; the competent cell method (K. Bott and G. A. Wilson, J. Bacteriol., 94:562 (1967)) and the protoplast method (M. Mandel and A. Higa, J. Mol. Biol., 53:159 (1970)) for bacteria belonging to the genus Bacillus; the protoplast method (M. Broker et al., BioTechniques, 5:516 (1987)) for yeast; and the lipofectin method (R. W. Malone et al., Proc. Natl. Acad. Sci. U. S. A., 86:6077 (1989)) and the calcium phosphate method (F. L. Graham and A. J. van der Eb, virology, 52:456 (1973)) for insect cells and mammalian cells. In addition, the electroporation method (refer to the BIORAD Company's brochure) can be used with all the cell types described above.

Basically, the DNA encoding the region to be expressed can be inserted into the plasmid or viral DNA capable of replicating in the host downstream from a strong promoter that functions in the host. If the gene to be expressed is missing the translation initiation codon, it needs to be added. When a prokaryotic cell is used as the host, the ribosome binding sequence (J. R. MacLaughlin et al., T. Biol. Chem., 256:11283 (1981)) is necessary. It is also possible to apply a method using a vector, which is not replicapable in the host and contains a part of the host chromosomal DNA, to effect a homologous recombination with the host chromosome, thereby integrating the vector into the host chromosome (JP-A-Hei 4-278092, D. J. King et al., Biochem. J., 281:317 (1992)). On the other hand, animal or plant bodies may be used as hosts instead of cultured cells. For example, compared with the case that cultured cells are used as hosts, the polypeptide may be recovered from the body fluid of the silkworms more efficiently by constructing a recombinant virus from BmNPV, which is a silkworm virus, and inoculating it into silkworms (H. Kawai and Y. Shimomura, Bioindustry, 8:39 (1991)). The recombinant polypeptide may be obtained by transplanting the mouse myeloma cells transformed with a recombinant pSV vector into the abdominal cavity of a SCID or nude mouse and recovering the polypeptide from the abdominal fluid of the mouse. It may also be possible to use as hosts transgenic animals (G. Wright et al., Bio/Technology, 9:830 (1991)) or transgenic plants (M. Owen et al., Bio/Technology, 10:790 (1992)) constructed with the DNA of the present invention.

In order to secrete the polypeptide of the present invention extracellularly, the signal peptide coding region of KDR can be used as it is if a eukaryotic cell is used as the host. If a bacterium is used as the host, the DNA encoding the signal peptide of a host's secreted polypeptide may be utilized. For example, the DNA encoding the signal peptide includes, as those for used in *E. coli*, outer membrane proteins such as OmpA or OmpF, phosphatases such as PhoA, and maltose binding protein MalB; as those for use in the genus Bacillus, the DNA encoding the signal peptide for amylases, alkaline phosphatases, and serine proteases, whose nucleotide sequences are known. If intracellular expression is desired, the signal peptide coding region except the initiation codon can be excluded. When an exogenous polypeptide is expressed at a high level in bacterial cells, inclusion bodies are often formed. If this is the case, the inclusion bodies are dissolved in an 8 M urea solution, diluted to a polypeptide concentration of several μg/ml, and then dialyzed to gradually remove the urea, thereby recovering several percents of activity of the polypeptide. It is also possible to suppress the formation of inclusion bodies by concurrently expressing *E. coli* thioredoxin at a high level in the bacterial cells.

The polypeptide of the present invention produced by the methods as described above can be purified through usual biochemical means, including, for example, ammonium sulfate precipitation, ion exchange chromatography, gel filtration, and hydrophobic chromatography. Since the polypeptide of the present invention has affinity to heparin, the affinity chromatography with heparin resin can be utilized. When it is produced as a fusion polypeptide with another polypeptide, it can be purified by taking advantage of the properties possessed by partner polypeptide (M. Uhlen et al., Methods Enzymol., 185:129 (1990)). For example, the purification can be carried out by affinity chromatography (F. H. Arnold, Bio/Technology, 9:151 (1991)) with protein A-Sepharose or protein G-Sepharose if the partner for the fusion polypeptide is the Fc domain of an antibody (E. Harlow and D. Lane, "Antibodies", Cold Spring Harbor Laboratory Press, 1988), with glutathione-Sepharose if it is glutathione transferase (GST) (D. B. Smith and F. S. Johnson, Gene, 67:31 (1988)), with chloramphenicol-Sepharose if it is chloramphenicol, and with $Ni^{2+}$-NTA (nitryltriacetic acid)-agarose if it is a histidine oligomer.

The fractions containing the polypeptide of the present invention can be detected by EIA or western analysis using antibodies reactive with the polypeptide. The antibodies reactive with the polypeptide of the present invention can be obtained by synthesizing the oligopeptide corresponding to the N-terminal 25–39 amino acid residues, conjugating with carrier proteins such as bovine serum albumin and KLH (keyhole lymphet hemocyanin), and immunizing rabbits or other animals using a standard method (E. Harlow and D. Lane, "Antibodies", Cold Spring Harbor Laboratory Press, 1988). It is also possible to obtain the antibodies reactive with the polypeptide of the present invention by producing in *E. coli* a fusion protein between the polypeptide of the present invention and another polypeptide, purifying the fusion protein by taking advantage of the partner polypeptide's properties, and by using it as the immunogen.

Since the polypeptide of the present invention binds to VEGF, this activity can be used as an index for the purification process. For example, a solution containing the non-purified polypeptide of the present invention is appropriately diluted and a 96-well polystyrene microtiter plate is coated with the solution, followed by blocking in the same manner as in preparing a antibody-coated plate for EIA. Since the thus-obtained plate specifically binds to VEGF, the binding can be detected by measuring the residual radioactivity in the wells using the $^{125}$I-labeled VEGF. A fraction from the chromatography used for purifying the polypeptide of the present invention is preincubated with $^{125}$I-VEGF and the mixture is placed into the wells of the plate to measure the residual radioactivity. If the fraction contains the polypeptide of the present invention, its presence can be confirmed because it will bind to VEGF during the preincubation, which will cause a competition with the polypeptide of the present invention on the surface of the plate, thereby reducing the biding of VEGF to the plate.

The polypeptide of the present invention inhibits the binding of VEGF to the VEGF receptor by binding to VEGF. Since the polypeptide of the present invention inhibits the VEGF activity, it blocks the proliferation of vascular endothelial cells caused by the VEGF stimulation and the enhancement of vascular permeability caused by VEGF. Furthermore, the polypeptide of the present invention blocks the neovascularization in vivo caused by VEGF, thereby inhibiting the tumor growth.

Therefore, the polypeptide of the present invention is useful as an agent for diagnosis or test of cancer and other diseases as well as a therapeutic agent for these diseases.

BEST MODE FOR CARRYING OUT THE INVENTION

Figure 1:
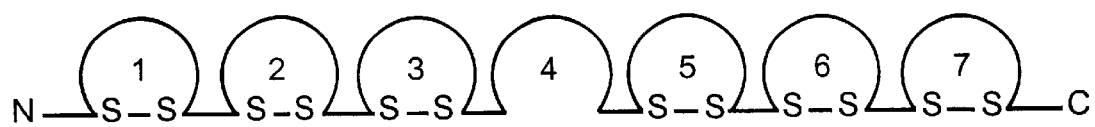
FIG. 1 schematically shows the constitution of the extracellular domain of KDR.

1. Construction of Recombinant Baculovirus Expressing KDR Extracellular Domain (EDK) Fragment 1.1 Preparation of cDNA from Human Umbilical Cord-derived Vascular Endothelial Cells (HUVEC)

One ml of ISOGEN (manufactured by Wako Pure Chemical Industries) was added to approximately $1 \times 10^7$ HUVEC cells (manufactured by Kurabo) and the cells were disrupted with a pestle. Further, 9 ml of ISOGEN was added thereto followed by shaking for 5 min. After adding 1 ml of chloroform to this solution, the mixture was shaken for 1 min and centrifuged at 10,000 rpm for 10 min to recover the supernatant, to which 1/10 volume of 3 M sodium acetate (pH 5.2) was added. To the resulting mixture was added 2.5 volume of ethanol to recover the precipitate following centrifugation. The precipitate was washed with 75% ethanol, dried, and dissolved in 100 µl heat-sterilized pure water. Thus, 102 µg of RNA was obtained. To this solution were added 1 µl of 10% SDS and 100 µl of "Oligotex-dT30 (manufactured by Takara Shuzo)". The resulting mixture was incubated at 65° C. for 5 min and then rapidly cooled in ice. This solution was mixed with 20 µl of 5 M sodium chloride and incubated at 37° C. for 10 min. The suspension thus obtained was centrifuged at 15,000 rpm for 15 min to recover the precipitate, which was resuspended in 100 µl of heat-sterilized pure water and incubated at 65° C. for 5 min. The suspension was centrifuged at 15,000 rpm for 15 min to recover the supernatant followed by ethanol precipitation. The dried precipitate was dissolved in 20 µl of heat-sterilized pure water. The resulting product was designated as HUVEC poly(A)$^+$ RNA. Subsequently, 100 µl of the oligo(dT)-primed HUVEC double-stranded cDNA solution was obtained using this solution and the CDNA synthesis kit manufactured by Pharmacia following the manual.

1.2 Cloning of DNA Encoding the KDR Extracellular Domain (EDK) Fragment

Using the HUVEC-derived CDNA obtained above as the template, PCR was performed with the following conditions.

TABLE 1

| Composition of the reaction mixture (in 50 µl) | PCR reaction condition |
| --- | --- |
| 5 µl LA-PCR buffer (Takara Shuzo)<br>0.25 mM each dNTPs<br>200 nM primer 1<br>200 nM primer 2<br>1 µl HUVEC cDNA<br>0.5 U LA-Taq polymerase (Takara Shuzo) | 1) 95° C., 1.5 min; 1 cycle<br>2) 95° C., 1 min; 58° C., 1 min; 72° C., 2.5 min; 35 cycles<br>3) 72° C., 5 min; 1 cycle |

The primer sequences are as follows:
Primer 1:
5'-TTCTCGGATCCTATAAATATGGAGAGCAAGGT GCTGCTGGCCGTC-3' (SEQ ID NO: 5)
Primer 2:
5'-TTCTCGAATTCTTAGTGGTGGTGGTGGTGG TGACGCTCTAGGACTGTGAGCTG-3' (SEQ ID NO: 6).

The underlined portion of "Primer" 1 corresponds to the N-terminal coding sequence of KDR, and that of "Primer 2" corresponds to the C-terminal coding sequence of the immunoglobulin-like domain 6.

Fifty µl of the reaction mixture was treated with an equal volume of chloroform in order to remove the mineral oil and the aqueous layer was recovered, to which 1 µl of 10% SDS was added. After incubation at 60° C. for 5 min, the solution was treated with an equal volume of TE-saturated phenol, an aqueous layer was recovered followed by ethanol precipitation to recover the DNA fragment. The dried precipitate was dissolved in 30 µl of TE and subjected to agarose gel electrophoresis. A DNA fragment of approximately 2.0 kbp was excised from the gel, and the DNA fragment was recovered using "Prep-A-Gene" (manufactured by BIORAD) according to the manual. The resulting DNA fragment was digested with BamHI. The reaction mixture was treated with an equal volume of TE-saturated phenol and the BamHI-digested DNA fragment was recovered from the aqueous layer using "Prep-A-Gene." 5'-Phosphorylation of the resulting BamHI-digested DNA fragment was carried out using "T4 Polynucleotide Kinase" (Takara Shuzo). The resulting reaction mixture was treated with an equal volume of TE-saturated phenol. The aqueous layer was recovered followed by ethanol precipitation to obtain the 5'-phosphorylated BamHI-digested DNA fragment.

Similarly, 1 µg of HincII/BAP-treated plasmid vector pUC118 DNA (Takara Shuzo) was digested with BamHI, the resulting reaction mixture was treated with an equal volume of TE-saturated phenol, and the BamHI-digested HincII/BAP-treated pUC118 DNA was recovered from the aqueous layer using "Prep-A-Gene." The DNA fragment and the plasmid DNA thus obtained were mixed at a molar ratio of 10:1 and ligation was performed (Ligation Kit manufactured by Takara Shuzo). E. coli JM109 competent cells (manufacturedby Takara Shuzo) were transformed by this ligation mixture, plated onto the 2 x TY culture medium (trypton 16 g, yeast extract 10 g, sodium chloride 5 g, and agar 1.5 g per 1 liter) containing 75 µg/ml ampicillin, and cultured overnight at 37° C. The ampicillin-resistant colonies that emerged on the plate were picked up with toothpicks and cultured overnight at 37° C. on 10 ml of 2×TY culture medium containing 50 µg/ml of ampicillin. The plasmid DNA was extracted from the bacterial cells recovered by the alkali method (according to the procedures described in "Molecular Cloning" supra) and named "pEDKH8".

1.3 Construction of Recombinant Transfer Vector for Preparing Recombinant Baculovirus Expressing KDR Extracellular Domain (EDK) Fragment 1.3.1 Construction of Recombinant Transfer Vector for Preparing Recombinant Baculovirus Expressing Immunoglobulin-like Domains 1 Through 6

Plasmid "pEDKH8" as obtained above was digested with BamHI and EcoRI, the resulting reaction mixture was treated with an equal volume of TE-saturated phenol, and the BamHI, EcoRI-digested DNA fragment was recovered from the aqueous layer using "Prep-A-Gene." Similarly, 1 µg of plasmid pVL1393 (PharMingen), a transfer vector for recombinant baculovirus, was digested with BamHI and EcoRI, the resulting reaction mixture was treated with an equal volume of TE-saturated phenol, and the BamHI, EcoRI-digested pVL1393 fragment was recovered from the aqueous layer using "Prep-A-Gene."

The DNA fragment and the plasmid DNA thus obtained were mixed at a molar ratio of 10:1 and ligation was performed. E. coli JM109 competent cells were transformed by this ligation mixture, plated onto the 2×TY culture medium containing 75 µg/ml ampicillin, and cultured overnight at 37° C. The ampicillin-resistant colonies that emerged on the plate were picked up with toothpicks, transferred into 15 µl of the PCR reaction mixture which was identical to the above-described one except for lacking the template to perform PCR as described above for 30 cycles. After the PCR, the reaction mixture was subjected to agarose gel electrophoresis, a single colony was isolated from the colonies that produced a 2.0 kbp band. This was named "pEDK22". This plasmid DNA was sequenced using Primer 1 or Primer 2 (according to the procedures described in "Molecular Cloning" supra) and approximately 150 nucleotides upstream and downstream from the fragment were examined. As a result, the sequence of the fragment was confirmed to be identical to the nucleotide sequence of the KDR extracellular domain (EDK)-coding DNA.

1.3.2 Construction of Recombinant Transfer Vector for Preparing Recombinant Baculovirus Expressing Immunoglobulin-like Domains 1 Through 3

Using plasmid "pEDKH22" obtained as above as the template, PCR was performed with the following conditions.

TABLE 2

| Composition of the reaction mixture (in 50 µl) | PCR reaction condition |
|---|---|
| 5 µl LA-PCR buffer (Takara Shuzo) | 4) 95° C., 1.5 min; 1 cycle |
| 0.25 mM dNTPs | 5) 95° C., 1 min; 58° C., 1 min; 72° C., 2.5 min; 35 cycles |
| 200 nM primer 1 | 6) 72° C., 5 min; 1 cycle |
| 200 nM primer 2 | |
| 1 µl HUVEC cDNA | |
| 0.5 U LA-Taq polymerase (Takara Shuzo) | |

The primer sequences are as follows:
Primer 1:
5'-TTCTCGGATCCTATAAATATGGAGAGCAAGGT GCT CTGGCCGTC-3' (SEQ ID NO: 5)
Primer 3:
5'-TTCTCGAATTCTTAGTGGTGGTGGTGGTGG TGAGATTCCATGCCACTMCC-3' (SEQ ID NO: 7).

The underlined portion of "Primer 3" corresponds to the C-terminal coding sequence of the immunoglobulin-like domain 3.

Fifty µl of the reaction mixture was treated with an equal volume of chloroform in order to remove the mineral oil and the aqueous layer was recovered, to which 1 µl of 10% SDS was added. After incubation at 60° C. for 5 min, the solution was treated with an equal volume of TE-saturated phenol, an aqueous layer was recovered followed by ethanol precipitation to recover the DNA fragment. The dried precipitate was dissolved in 30 µl of TE and subjected to agarose gel electrophoresis. A DNA fragment of approximately 1.0 kbp was excised from the gel, and the DNA fragment was recovered using "Prep-A-Gene" according to the manual. The recovered DNA was digested with BamHI and EcoRI, the resulting reaction mixture was treated with an equal volume of TE-saturated phenol, and the BamHI, EcoRI-digested DNA fragment was recovered from the aqueous layer using "Prep-A-Gene."

Similarly, 1 µg of plasmid pVL1393, a transfer vector for recombinant baculovirus, was digested with BamHI and EcoRI, the resulting reaction mixture was treated with an equal volume of TE-saturated phenol, and the BamHI, EcoRI-digested pVL1393 fragment was recovered from the aqueous layer using "Prep-A-Gene."

The DNA fragment and the plasmid DNA thus obtained were mixed at a molar ratio of 10:1 and ligation was performed. E. coli JM109 competent cells were transformed by this ligation mixture, plated onto the 2×TY culture medium containing 75 µg/ml ampicillin, and cultured overnight at 37° C. The ampicillin-resistant colonies that emerged on the plate were picked up with toothpicks, transferred into 15 µl of the PCR reaction mixture which was identical to the above-described one except for lacking the template to perform PCR as described above for 30 cycles. After the PCR, the reaction mixture was subjected to agarose gel electrophoresis, single colonies were isolated from the ones that produced a 1.0 kbp band. This was named "pbEDK13."

The E. coli cells harboring these plasmids were cultured in 100 ml of the 2×TY medium containing 50 µg/ml ampicillin overnight at 37° C. The plasmid DNAS were extracted from the recovered cell bodies using the alkali method, purified with an ion exchange column according to the manual (Diagen GimbH manufactured by Qiagen), and dissolved in 200 µl each of TE, to give approximately 100 µg each of plasmid DNA.

1.4 Production of Recombinant Baculovirus Expressing EDK Fragment

Sf9 cells (manufactured by Invitrogen Corp.) cultured in the TMN-FH medium (manufactured by PharMingen) at an 80% confluency were detached by pipetting, inoculated at $2 \times 10^6$ cells per 60 mm dish, and allowed to adsorb onto the surface by standing for 30 min. Then, the medium was replaced with 1.5 ml of Ex-Cell 400 (manufactured by IwakiGlass), which is a serum-free medium. Twelve µl of the solution containing 4 µl (2 µg) of "pbEDK13" and 2 µl (20 ng) of the deleted baculovirus DNA (BaculoGold manufactured by PharMingen) was mixed with 12 µl of the solution made by diluting Lipofectin two-fold in sterilized pure water. After the mixture. was allowed to stand for 15 min, the total volume of 24 µl was added to the above-described dish and mixed. The dishes were standing-cultured in a humidified box at 27° C. for one day, and were standing-cultured at 27° C. for 4 days after replacing the medium with 2.5 ml TMN-FH. The medium was recovered and the supernatant obtained by centrifugation was prepared as the original virus stock. This recombinant virus was designated "BEDK13M". The plaque assay performed according to the manual of Invitrogen Corp. revealed that the virus had a titer of approximately $3 \times 10^6$. The thus-obtained original virus stock was amplified by 3 steps according to the manual of Invitrogen Corp. to give about 30 ml of the virus solution (having a titer of about $5 \times 10^7$/ml).

In the same manner, a recombinant virus "BEDK16" was prepared using "pEDKH22."

2. Analysis of the Expression Products from the Recombinant Virus-infected Sf9 Cells 2.1 Covalently Cross-linked Products with $^{125}$I-VEGF$_{165}$ Sf9 cells were allowed to be infected with the recombinant virus "BEDK13M" at m.o.i. of 5 (m.o.i. means the ratio of virus particles to cell number) and cultured for 7 days. To the resulting culture supernatant was added 200,000 cpm of $^{125}$I-VEGF$_{165}$ (100,000 cpm/ng, Amersham) and incubated in 100 µl of PBS-0.1% BSA for 1.5 hr at room temperature. This solution was mixed with 4 µl of 25 mM disuccinylsuberate/dimethylsulfoxide/PBS, and, after incubation at room temperature for 40 min, 1/10 volume of 1 M Tris-HCl (pH 6.8) was added. These samples were subjected to SDS-polyacrylamide gel electrophoresis under non-reducing conditions according to Laemmli and the signal was detected by autoradiography (FIGS. 2A and 2B).

Figure 2A:
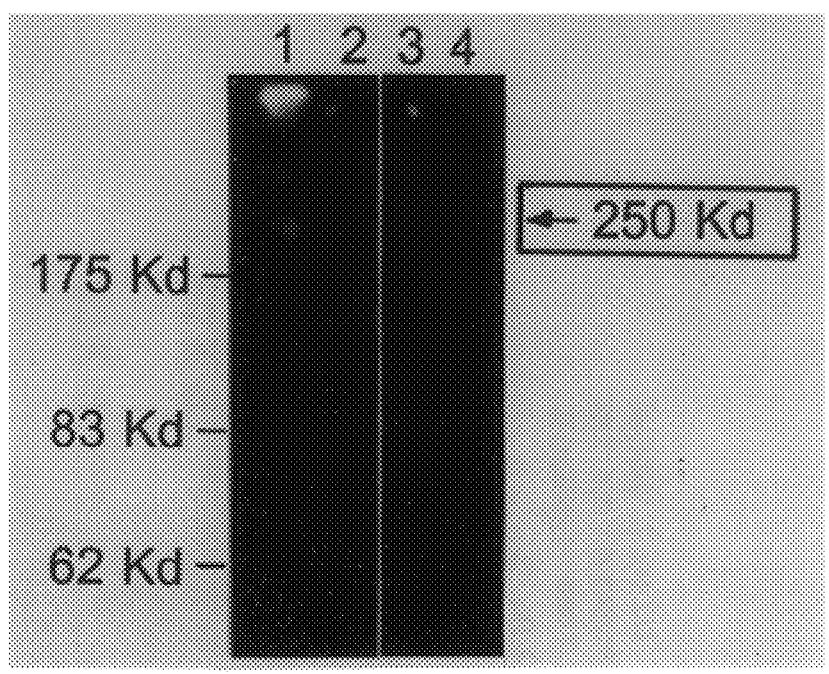
FIG. 2A shows the autoradiography following the electrophoresis of the covalently cross-linked products between the cells infected with an EDK16-expressing recombinant baculovirus and $^{125}$I-VEGF$_{165}$. Lane 1 shows the result of cells infected with the recombinant virus EDK16. Lane 2 shows the result of adding labeled and non-labeled VEGF$_{165}$ to cells infected with EDK16. Lane 3 shows the result from cells infected with a control virus. Lane 4 shows the result of adding labeled and non-labeled VEGF$_{165}$ to cells infected with the control virus.
Figure 2B:
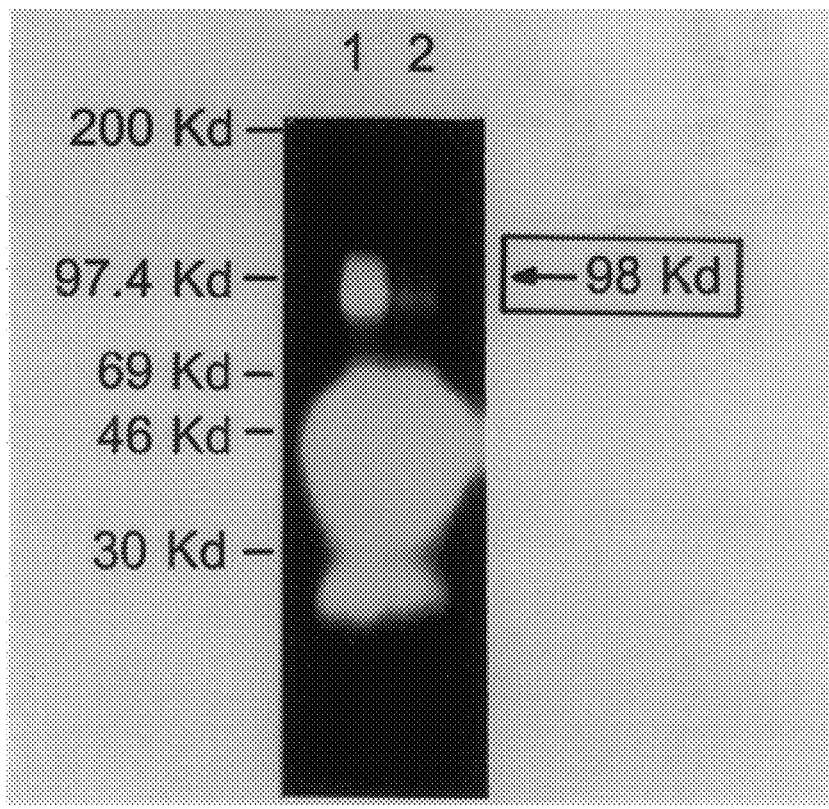
FIG. 2B shows an autoradiography following the electrophoresis of the covalently cross-linked products between cells infected with an EDK13-expressing recombinant baculovirus and $^{125}$I-VEGF$_{165}$. Lane 1 shows the result of cells infected with recombinant virus EDK13M. Lane 2 shows the result obtained when labeled and non-labeled VEGF$_{165}$ were added to cells infected with EDK13M. Lane 3 shows a cross-linked product between a dimer of EDK13 and a dimer of VEGF$_{165}$.

As a result, a covalently cross-linked product of molecular weight of 98,000 was detected (lane 1 in FIG. 2B), while no covalently cross-linked product was detected in the culture supernatant of the cells infected with the control virus constructed using the recombinant virus, in which the DNA encoding FLT extracellular domain that is a VEGF receptor had been inserted in the opposite direction to the promoter (lane 3 in FIG. 2A). Lane 1 in FIG. 2A shows the result of the culture supernatant of the 7-day cultured cells infected with "BEDK16" as a positive control at m.o.i. of 5 and lane 3 shows the result of the above-described control virus-infected cells. Lanes 2 and 4 show the results obtained by adding 100-fold non-labeled VEGF$_{165}$ (R&D) to the system of lanes 1 and 3.

The 250 Kd band indicated by an arrow in the figure corresponds to the covalently cross-linked product between a dimer of the polypeptide consisting of the immunoglobulin-like domains 1 through 6 of EDK and a dimer of VEGF$_{165}$. Lane 1 in FIG. 2B shows the result of the culture supernatant of the cells infected with "BEDK13M" and lane 2 shows the result obtained by adding 100-fold non-labeled VEGF$_{165}$ (R&D).

Since the molecular weight of the VEGF$_{165}$ (R&D) dimer is 42,000, it is subtracted from the molecular weight of 98,000 of the covalently cross-linked product to give 56,000. The molecular weight estimated from the amino acid sequence is about 56,000. Therefore, it was confirmed that the "BEDK13M"-infected cells expressed the polypeptide consisting of the immunoglobulin-like domains 1 through 3 of EDK. The polypeptide expressed by "BEDK13M" was designated as "EDK13."

2.2 Nucleotide Sequence Analysis of the Insert DNA in the Recombinant Transfer Vector Nucleotide sequences were determined in order to confirm the cloned DNA's sequences in the plasmid "pbEDK13" which revealed that the nucleotide sequence of the part of the insert DNA in "pbEDK13", which corresponds to the immunoglobulin-like domains 1 through 3 of the KDR extracellular domain, differs in only two residues from the sequence of KDR gene (SEQ ID NO: 1) reported by Bruce I. Terman (in SEQ ID NO: 1, T at position 382 was replaced with A and T at position 636 was replaced with C). As a result, serine at position 109 of the amino acid sequence was replaced with threonine.

2.3 Inhibition of the Biological Activities of VEGF

Figure 3:
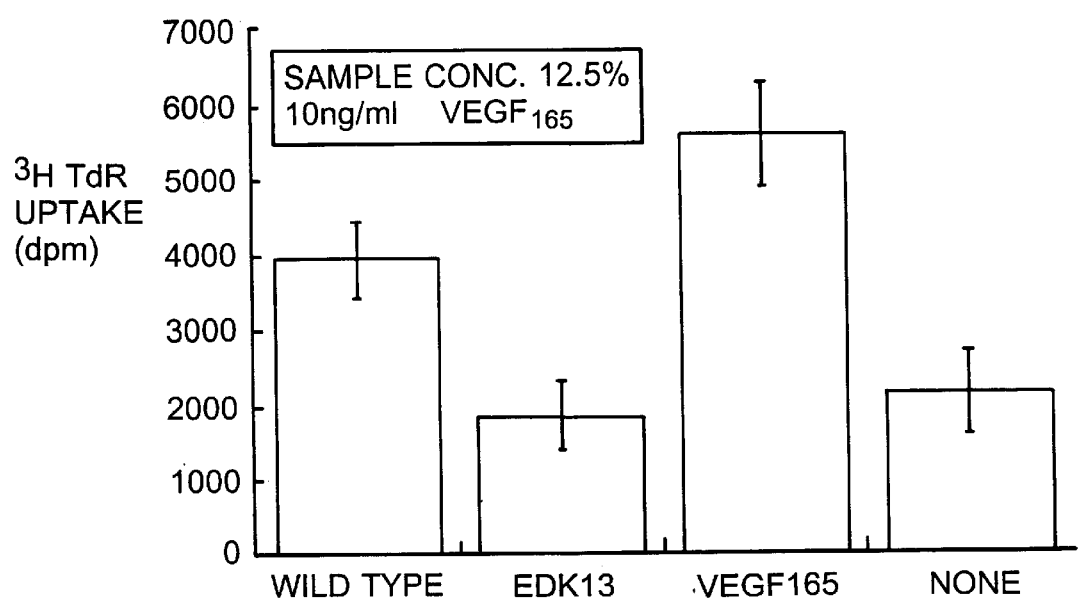
FIG. 3 shows the inhibition of the VEGF-dependent thymidine uptake in HUVEC by the culture supernatants of EDK13-expressing cells.

The "EDK13"-expression culture supernatant was examined for inhibition of enhancement by VEGF of the thymidine uptake of the human umbilical cord-derived vascular endothelial cells (HUVEC). HUVEC cells were inoculated on a 96-well collagen plate (manufactured by Iwaki Glass) at 3,000 cells/well/100 µl (EGM-UV medium manufactured by Kurabo) and cultured at 37° C., 5% $CO_2$, for 24 hr. The cells were washed twice with a washing medium, 50 µl of 20 ng/ml VEGF$_{165}$ and 50 µl of the sample were added there to followed by culturing for 4 days. Ten µl of 50 µCi/2 nmoles/ml of $^3$H-thymidine (Amersham) was added to each well and incubated for another 24 hr. After washing twice with PBS, the cells were detached by trypsin/EDTA and recovered on a glass filter by Cell Harvester (manufactured by Cambridge Technology, Inc.) to measure radioactivity with a scintillation counter (FIG. 3). Compared with the wild type virus-infected culture supernatant used as the control, the "EDK13"-expression culture supernatant showed a significant inhibition of the VEGF-dependent thymidine uptake. The results elucidated that "EDK13" inhibited enhancement by VEGF of the thymidine uptake by HUVEC, i.e., the enhancement of DNA synthesis.

3. Confirmation of the Function of Fusion Protein Between Fragments of the Extracellular Region of KDR (EDK) and IgG-Fc Region 3.1 Expression of Fusion Protein Between Fragments of the Extracellular Region of KDR and IgG-Fc Region in the *Bombyx mori* Body Fluid 3.1.1 Preparation of DNA Encoding EDK Fragments Using plasmid "pEDKH22" DNA as obtained above as the template, PCR was performed under the following conditions to amplify DNA fragments encoding the immunoglobulin-like domains 1 and 2 or the immunoglobulin-like domains 1 through 3 of EDK.

TABLE 3

Amplification of DNA encoding the immunoglobulin-like domains 1 and 2 of EDK

| Composition of the reaction mixture (in 100 µl) | PCR reaction condition |
|---|---|
| 10 µl LA-PCR buffer (Takara Shuzo)<br>0.25 mM dNTPs<br>200 nM primer 1<br>200 nM primer 4<br>1 µg EDKH22<br>1.0 U LA-Taq polymerase (Takara Shuzo) | 1) 96° C., 2 min; 1 cycle<br>2) 95° C., 1 min; 60° C., 1 min; 72° C., 30 min; 30 cycles<br>3) 72° C., 10 min; 1 cycle |

The sequence of Primer 1 was shown above. The sequence of Primer 4 is as follows:
Primer 4:
5'-TTTGTCACAATTTGGGCTCCGGACTCAGAAC CACATCATA-3' (SEQ ID NO: 8).

The portion of Primer 4 with the wavy underline corresponds to the sequence (antisense strand) encoding five amino acids at the N-terminus of the hinge region of human IgG1-Fc region, and that with the straight underline corresponds to the sequence (antisense strand) encoding the immunoglobulin-like domain 2 (205 to 211) of EDK.

TABLE 4

Amplification of DNA encoding the immunoglobulin-like domains 1 through 3 of EDK

| Composition of the reaction mixture (in 100 µl) | PCR reaction condition |
|---|---|
| 10 µl LA-PCR buffer (Takara Shuzo)<br>0.25 mM dNTPs<br>200 nM primer 1<br>200 nM primer 5<br>1 µg EDKH22<br>1.0 U LA-Taq polymerase (Takara Shuzo) | 1) 96° C., 2 min; 1 cycle<br>2) 95° C., 1 min; 60° C., 1 min; 72° C., 1 min; 30 cycles<br>3) 72° C., 10 min; 1 cycle |

The sequence of Primer 1 was shown above. The sequence of Primer 5 is as follows:
Primer 5:
5'-TTTGTCACAATTGGCTCAGATTCCATGCCA CTTCCA-3' (SEQ ID NO: 9).

The portion of Primer 5 with the wavy underline corresponds to the sequence (antisense strand) encoding five amino acids at the N-terminus of the hinge region of human IgG1-Fc domain, and that with the straight underline corresponds to the sequence (antisense strand) encoding the immunoglobulin-like domain 3 (313 to 319) of EDK.

In a similar manner as described above, from each PCR solution was obtained the purified DNA fragment (0.6 Kbp) encoding the immunoglobulin-like domains 1 and 2 of EDK, or that (0.9 Kbp) encoding the immunoglobulin-like domains 1 through 3 of EDK, respectively, and they were independently dissolved in 20 µl of TE buffer [10 mM Tris-HCl (pH 7.5) and 1 mM EDTA-2Na].

3.1.2 Preparation of DNA Fragments Encoding Human IgG1-Fc Region

Human lymphobalstoma IM9 cell line (Dainihon Pharmaceutical Co.) was cultured in the PRMI1640 medium (GIBCO BRL). From 4×10$^7$ cells, cDNA solution (100 µl)

was prepared in the same manner as described above, and DNA fragments of human IgG1-Fc were amplified by PCR in two steps.

TABLE 5

Amplification of DNA encoding human IgG1-Fc

| Composition of the reaction mixture (in 100 μl) | PCR reaction condition |
|---|---|
| 10 μl LA-PCR buffer (Takara Shuzo)<br>0.25 mM dNTPs<br>200 nM primer 6<br>200 nM primer 7<br>1 μl IM9 cDNA<br>1.0 U LA-Taq polymerase (Takara Shuzo) | 1) 94° C., 2 min; 1 cycle<br>2) 94° C., 1 min; 60° C., 1 min; 72° C., 1 min; 60 cycles<br>3) 72° C., 10 min; 1 cycle |

Sequences of Primer 6 and Primer 7 are as follows:
Primer 6:
5'-TCTTGTGACAAAACTCACACATGC-3' (SEQ ID NO: 10)
Primer 7:
5'-CGGAGACAGGGAGAGGCTCTTCTG-3' (SEQ ID NO: 11).

Primer 8 and Primer 9 were added to the above-described PCR reaction solution to a concentration of 200 nM, and a second PCR was performed by 15 cycles under the conditions 2) followed by 1 cycle under the condition 3) in Table 5.

Sequences of Primers 8 and Primer 9 are as follows:
Primer 8:
5'-GAGCCCAAATCTTGAGACAAA-3' (SEQ ID NO: 12)
Primer 9:
5'-TTCTTCTAGATTAGTGGTGGTGGTGGTGGTG TTTACCCGGAGACAGGGA-3' (SEQ ID NO: 13).

Primer 8 corresponds to the sequence encoding the N-terminal amino acids of human IgG1-Fc. The portion of Primer 9 with the dotted underline corresponds to the restriction enzyme XbaI recognition site, that with the double underline to the stop codon (antisense strand), that with the straight underline to the codons for six histidine residues (antisense strand), and that with the wavy underline to the sequence encoding the C-terminal amino acids of human IgG1-Fc (antisense strand).

In a similar manner as described above, from each PCR solution were obtained the purified DNA fragments of 0.7 Kbp each encoding the human IgG1-Fc, and independently dissolved in 20 μl of TE buffer [10 mM Tris-HCl (pH 7.5) and 1 mM EDTA-2Na].

3.1.3 Preparation of DNA Encoding the Fusion Protein Between EDK Fragment and Human IgG1-F PCR was performed under the following conditions to join the immunoglobulin-like domains 1 and 2 (EDK12) DNA or the immunoglobulin-like domains 1 through 3 (EDK13) DNA of EDK obtained as described above with the human IgG1-Fc (hIgG1-Fc).

TABLE 6

Fusion reaction between EDK12 DNA and human IgG1-Fc (hIgG1-Fc) DNA

| Composition of the reaction mixture (in 100 μl) | PCR reaction condition |
|---|---|
| 10 μl LA-PCR buffer (Takara Shuzo) | 1) 95° C., 2 min; 1 cycle<br>2) 94° C., 1 min: slowly cooled |

TABLE 6-continued

Fusion reaction between EDK12 DNA and human IgG1-Fc (hIgG1-Fc) DNA

| Composition of the reaction mixture (in 100 μl) | PCR reaction condition |
|---|---|
| 0.25 mM dNTPs<br>200 nM primer 1<br>200 nM primer 9<br>2 μl EDK12 DNA<br>2 μl hIgG1-Fc DNA<br>1.0 U LA-Taq polymerase (Takara Shuzo) | to 50° C. in 15 min, then 1 min;<br>72° C., 1 min; 3 cycles<br>3) 94° C., 1 min: 60° C., 1 min; 72° C., 1 min; 30 cycles<br>4) 72° C., 10 min; 1 cycle |

TABLE 7

Fusion reaction between EDK13 DNA and human IgG1-F DNA

| Composition of the reaction mixture (in 100 μl) | PCR reaction condition |
|---|---|
| 10 μl LA-PCR buffer (Takara Shuzo)<br>0.25 mM dNTPs<br>200 nM primer 1<br>200 nM primer 9<br>2 μl EDK13 DNA<br>2 μl hIgG1-Fc DNA<br>1.0 U LA-Taq polymerase (Takara Shuzo) | 1) 95° C., 2 min; 1 cycle<br>2) 94° C., 1 min: slowly cooled to 50° C. in 15 min, then 1 min;<br>72° C., 1 min; 3 cycles<br>3) 94° C., 1 min: 60° C., 1 min; 72° C., 1 min; 30 cycles<br>4) 72° C., 10 min; 1 cycle |

In a similar manner as described above, from each PCR reaction solution were obtained the purified EDK12/hIgG1-F fusion DNA of 1.3 Kbp and the purified EDK12/hIgG1-F fusion DNA of 1.6 Kbp, respectively.

3.1.4 Preparation of Recombinant Expression Virus Functioning in Bombyx mori

In the same manner as described above, both termini of each DNA fragment described above were digested with restriction enzymes EcoRI and XbaI, and inserted to Bombyx mori nuclear polyhederosis virus transfer vector pBM0050 (S. Maeda, Gene transfer vectors of a baculovirus, Bombyx mori, and their use for expression of foreign genes in insect cells, Invertebrate cell system applications, p. 167, Vol. I, Ed. by J. Mitsuhashi, CRC Press, 1989) previously digested with EcoRI and XbaI to obtain the respective purified recombinant plasmids. Then, in order to obtain recombinant virus, these plasmid DNAs and DNA of CPd virus, a cysteine protease-deficient mutant of the Bombyx mori nuclear polyhedrosis virus (T. Suzuki et al., Journal of General Virology, 78, p. 3073, 1997, Japanese Patent Laid-Open Publication No. Hei 7-303488) were co-transfected to Bombyx mori-derived BoMo15AIIc cells (J. Kobayashi, et al., Cytotechnology 8, p. 103, 1992) using the lipofectin reagent (GibcoRRI) according to the manual.

Then, EIA was performed applying the culture supernatant of single virus clone obtained by the limiting dilution to Immulon 2 strip (Dinatech) pre-coated with $VEGF_{121}$ (S. Kondo et al., BBA, 1243, p. 195, 1995) and using POD-labeled anti-human IgG antibody (MBL) as the secondary antibody to select color-developed clones. Furthermore, since the culture supernatant was believed to contain the recombinant virus, it was infected to BoMo15AIIc cells to propagate to the density of about $10^8$ cells/ml.

3.1.5 Preparation of Anti-EDK Peptide Serum

Peptide comprising 15 amino acid residues from proline at position 5 in the amino acid sequence of EDK was synthesized using MAP resin, and immunized to rabbit every 2 week three times to obtain anti serum.

3.1.6 Inoculation of Virus to *Bombyx mori* Larva

The culture supernatant containing each recombinant virus was mixed with diet, and fed to *Bombyx mori* larvae of the fifth instar at the dose of $10^4$ to $10^5$ viruses per larva. The body fluid was recovered from them after 5- to 6-day feeding and phenylthiourea was added to the body fluid to prevent melanization. It was then stored at −80° C.

Figure 4A:
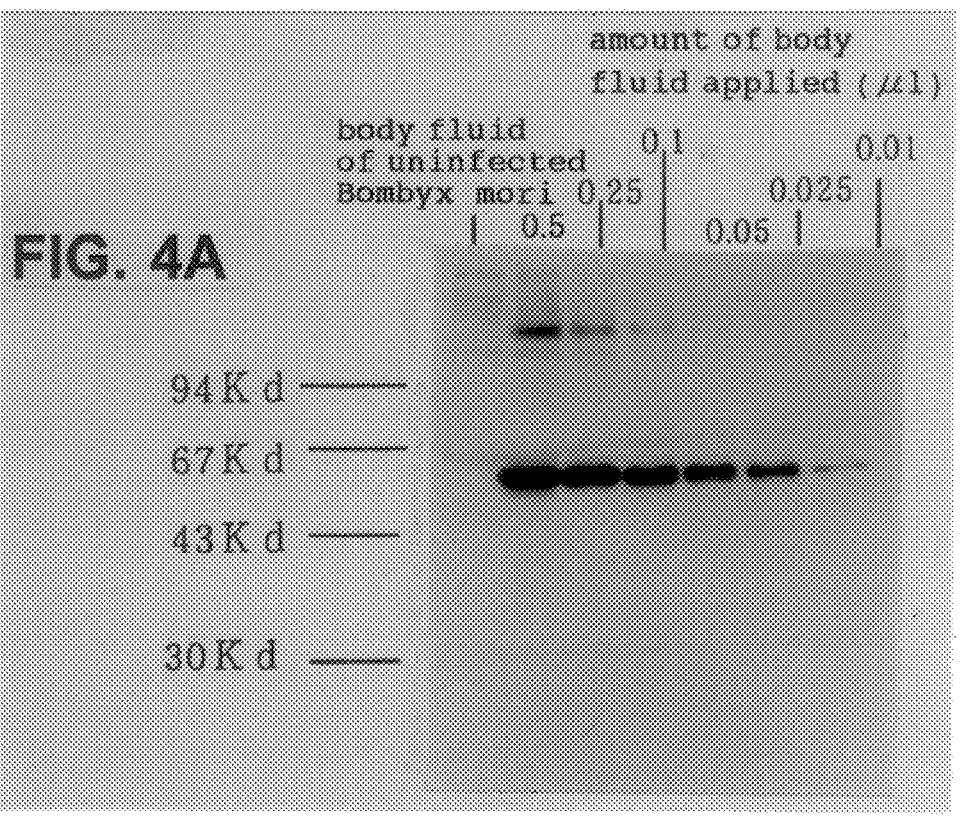
FIG. 4A shows the results of the western blotting using anti-EDK peptide serum from body fluids of *Bombyx mori* infected with a recombinant virus carrying an EDK12/hIgG-Fc fused gene.
Figure 4B:
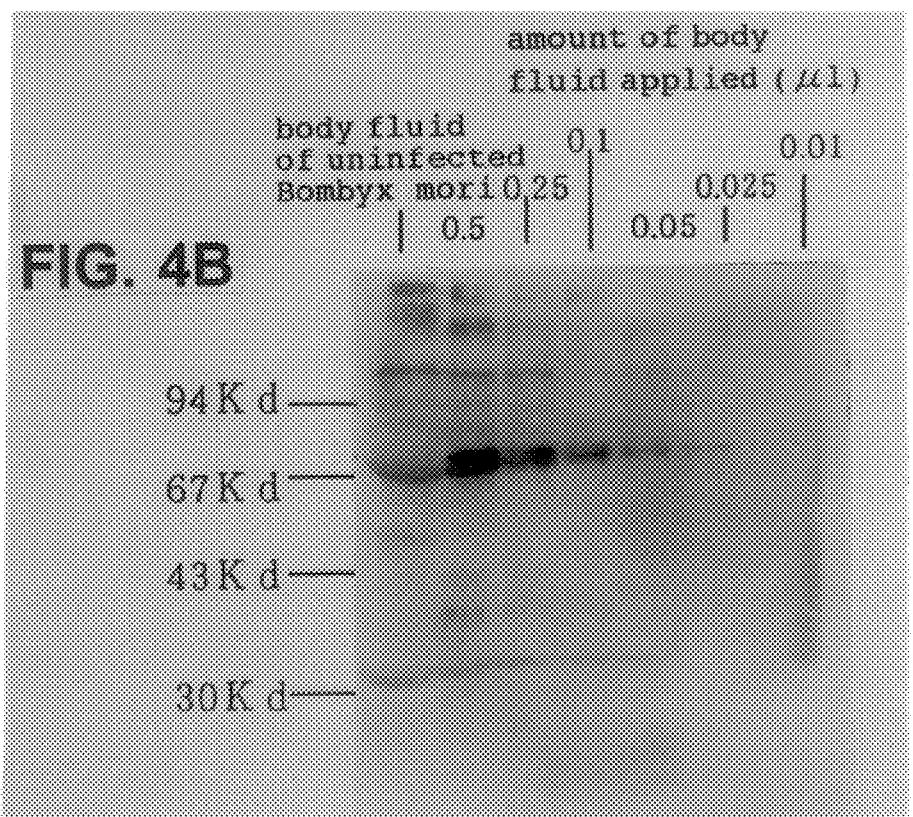
FIG. 4B shows the results of the western blotting using anti-EDK peptide serum from body fluids of *Bombyx mori* infected with a recombinant virus carrying an EDK13/hIgG-Fc fused gene.

3.1.7 Confirmation of Expression in *Bombyx mori* Larva and Identification of Expression Product According to the method described in "J. Sambrook, E. F. Fritsch and T. Maniatis, Molecular Cloning: A; laboratory manual (2nd edition), ed. by N. Ford et al., p. 18,1–p.18.75, Cold Spring Harbor Laboratory Press, New York (1989)", these samples were subjected to SDS-polyacrylamide gel electrophoresis followed by the Western blotting analysis using a 200-fold diluted anti-EDK peptide antiserum, revealing the formation of specific immunoreaction products corresponding to the predicted molecular weight which were not found in the body fluid of control larvae. That is, in the case of recombinant virus transformed with EDK12/hIgG-Fc fusion DNA, immunoreaction band corresponding to the molecular weight of about 55,000 was observed, and in the case of recombinant virus transformed with EDK13/hIgG-Fc fusion DNA immunoreaction band corresponding to the molecular weight of about 65,000 was detected (FIGS. 4A and 4B). From these results, the expression of EDK fragments was definitely identified. Also, EDK12/hIgG-Fc and EDK13/hIgG-Fc fusion proteins were designated VK12H and VK13H, respectively.

3.1.8 Purification of VK12H and VK13H from *Bombyx mori* Body Fluid

Figure 5:
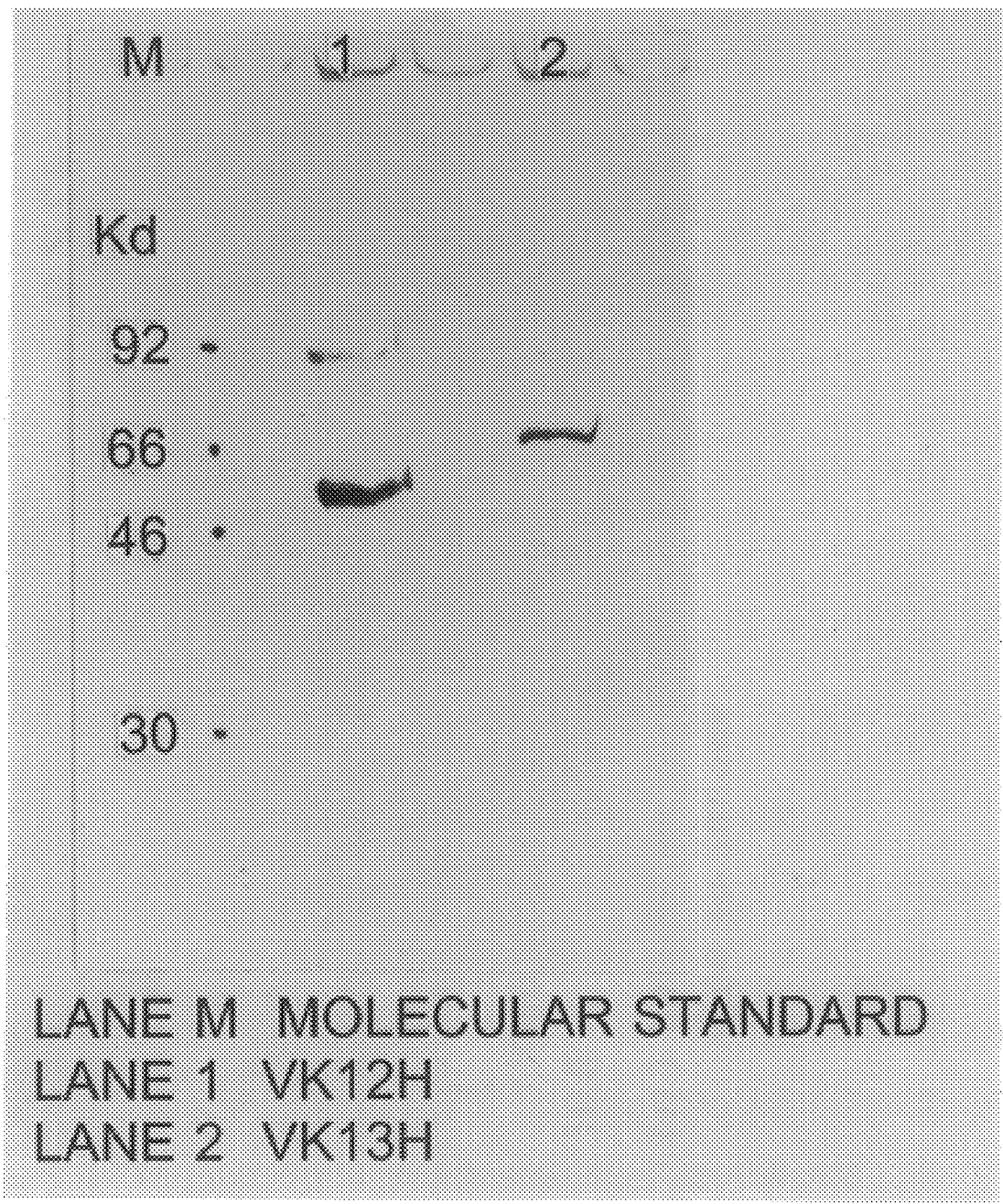
FIG. 5 shows the SDS-PAGE patterns of purified VK12H and purified VK13H.

All procedures were carried out at the temperature kept at 0 to 4° C. *Bombyx mori* body fluid recovered and stored was dissolved at room temperature, centrifuged at 15,000 rpm for 10 min, and the supernatant was filtered through a filter of pore size of 0.45 μm to remove insoluble materials. To this supernatant was added each reagent stock solution to the final concentrations of 20 mM for Tris-HCl (pH 8.0), 150 mM for KCl, 0.1% for NP-40 and 1 mM for imidazole-HCl (pH 8.0). This solution was applied onto a column of Hi-Trap Chelating/$CU^{2+}$ (Pharmacia), washed with the same buffer, then with the same buffer containing 40 mM imidazole-HCl (pH 8.0). Elution was performed using 0.3 M imidazole-HCl (pH 8.0)/0.5 M KCl. SDS-PAGE of the recovered protein indicated the purification of proteins corresponding to the bands observed by the Western blotting analysis (FIG. 5).

3.1.9 Confirmation of Binding Ability of Purified VK12H and VK13H to VEGF

Figure 6:
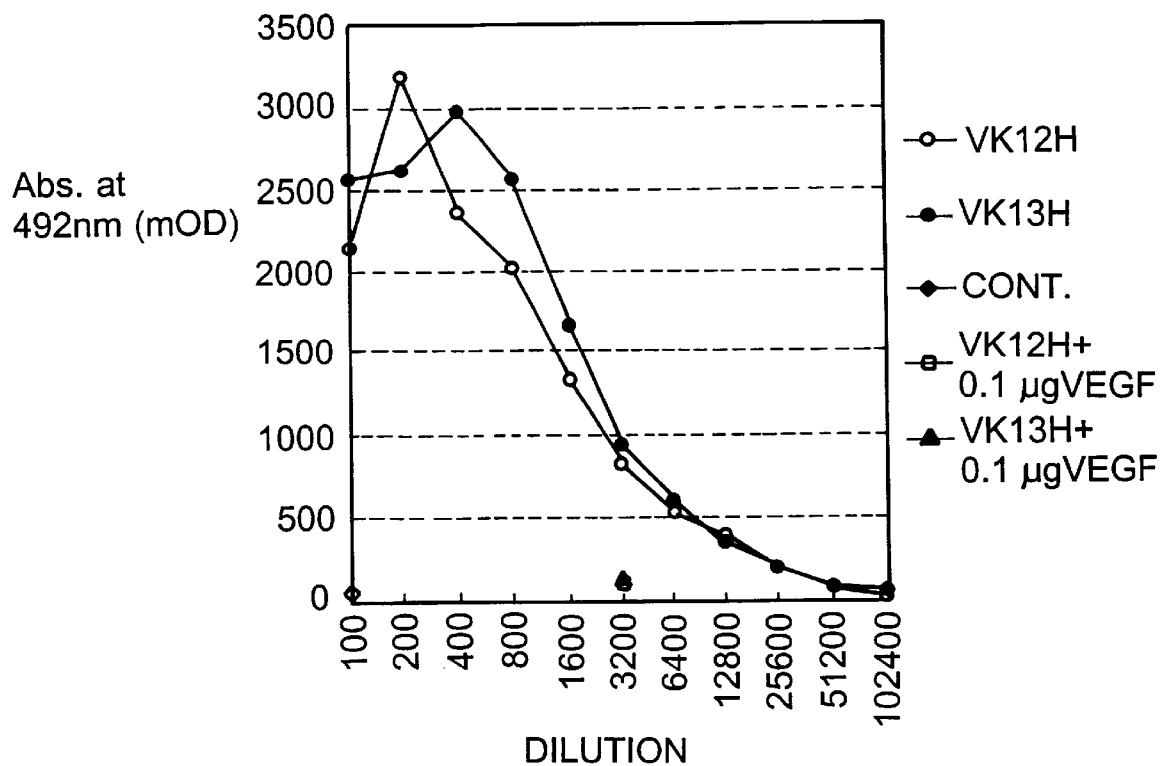
FIG. 6 shows binding abilities of purified VK12H and purified VK13H to a VEGF-coated plate.
Figure 6:
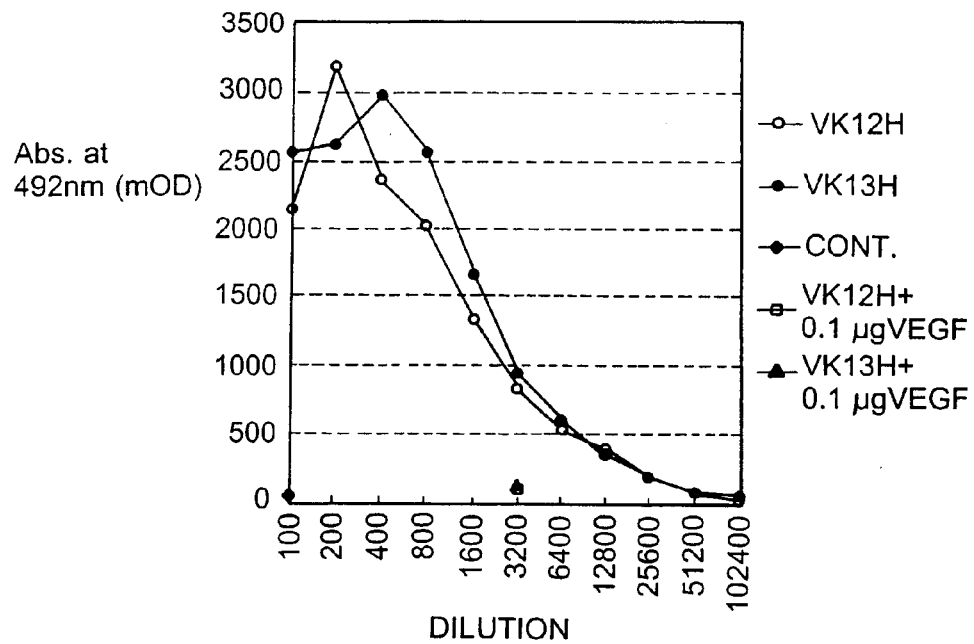

A solution (100 μl) of 100 ng $VEGF_{121}$/ml phosphate-buffered saline (PBS) was placed into each well of Immulon 2 strip and allowed to stand at 4° C. overnight. The solution in each well was discarded and 1% bovine serum albumin (BSA)/PBS (300 μl) was added therefor. The plate was incubated at room temperature for 2 h for blocking. Then, a diluted solution (100 μl) of purified VK12H or VK13H was added to each well, the plate was allowed to stand at room temperature for 1 h, and wells were then washed with 0.1% BSA/PBS six times. A POD-labeled anti-human IgG antibody (MBL) (100 μl) which had been diluted 1,000 fold with 0.1% BSA/PBS was added to each well, allowed to stand at room temperature for 1 h, and then the wells were washed six times with 0.1% BSA/PBS. A solution (100 μl) of 10 mM sodium acetate (pH 5.2), 0.15% hydrogen peroxide, and ortthophenylene diamine (OPD) (Wako Pure Chemical) (one tablet/20 ml) was added to each well to develop color for 30 min. After the reaction was terminated by adding 2 N sulfuric acid (100 μl), the absorbance at 492 nm was measured (FIG. 6). As a result, the VEGF-coated plate did not develop color at all when a 100-fold diluted body fluid of *Bombyx mori* infected with non-recombinant virus or a human IgG1 (BioPur AG, #10-3 1-1212, Swiss) (5 μg/ml) was added as the control, while it strongly develop color when purified VK12H and VK13H were used. Furthermore, the color development was inhibited by the externally added $VEGF_{165}$ (R&D) in excess. These results indicate that VK12H and VK13H specifically bind to VEGF. From these results, it has been proved that the fusion protein between the immunoglobulin-like domains 1 and 2 of the extracellular region of KDR and the human IgG1-Fc, and that between the immunoglobulin-like domains 1 through 3 of the extracellular region of KDR and the human IgG1-Fc are capable of binding to VEGF.

Industrial Applicability

The polypeptides of the present invention can be utilized in treating diseases accompanying pathological neovascularization, such as solid tumors, because they can inhibit the VEGF-stimulated neovascularization. In addition, since they are constituted by human-derived amino acids, they are unlikely to trigger antibody production when administered. Furthermore, since they have smaller molecular weights than the conventional polypeptides (R. L. Kendal and K. A. Thomas, Proc. Natl. Acad. Sci. U.S.A., 90:10705 (1993)), it is easier to express them using recombinant DNA techniques, and they infiltrate into diseased sites more quickly.

---

What is claimed is:

1. A DNA encoding a polypeptide comprising a KDR fragment comprising immunoglobulin-like domain 1 and immunoglobulin-like domain 2 of KDR, wherein the polypeptide lacks immunoglobulin-like domains 3 through 7 of KDR.

2. The DNA of claim 1, wherein the polypeptide comprises amino acid residues 1 to 214 of SEQ ID NO: 14.

3. A vector containing the DNA of claim 1.

4. A cultured cell comprising the DNA of claim 1 and which expresses the polypeptide.

5. A method of producing a polypeptide, comprising culturing the cell of claim 4 under conditions appropriate for expressing said DNA.

6. The DNA of claim 1, wherein the polypeptide further comprises an Fc domain of an immunoglobulin.

7. A DNA encoding a fusion polypeptide, wherein the polypeptide comprises (a) an Fc domain of an immunoglobulin, and (b) a KDR fragment comprising immunoglobulin-like domain 1 and immunoglobulin-like domain 2 of KDR, wherein the polypeptide lacks immunoglobulin-like domains 3 through 7 of KDR.

8. The DNA of claim 7, wherein the KDR fragment comprises amino acid residues 1 to 214 of SEQ ID NO: 14.

9. A vector comprising the DNA of claim 7.

10. A cultured cell comprising the DNA of claim 7 and which expresses the polypeptide.

11. A method of producing a polypeptide, comprising culturing the cell of claim 10 under conditions appropriate for expressing said DNA.

12. A polypeptide comprising a KDR fragment comprising immunoglobulin-like domain 1 and immunoglobulin-like domain 2 of KDR, wherein the polypeptide lacks immunoglobulin-like domains 3 through 7 KDR.

13. The polypeptide of claim 12, wherein the polypeptide comprises amino acid residues 1 to 214 of SEQ ID NO: 14.

14. The polypeptide of claim 12, wherein the polypeptide further comprises an Fc domain of an immunoglobulin.

15. A fusion polypeptide comprising (a) an Fc domain of an immunoglobulin, and (b) a KDR fragment comprising immunoglobulin-like domain 1 and immunoglobulin-like domain 2 of KDR, wherein the polypeptide lacks immunoglobulin-like domains 3 through 7 of KDR.

16. The fusion polypeptide of claim 15, wherein the KDR fragment comprises amino acid residues 1 to 214 of SEQ ID NO: 14.

* * * * *

UNITED STATES PATENT AND TRADEMARK OFFICE
CERTIFICATE OF CORRECTION

PATENT NO.    : 6,348,333 B1
DATED         : February 19, 2002
INVENTOR(S)   : Mikio Niwa et al.

It is certified that error appears in the above-identified patent and that said Letters Patent is hereby corrected as shown below:

Title page,
Item [56], References Cited, U.S. PATENT DOCUMENTS, "5,952,199" reference, replace "Smith" with -- Smyth --.
OTHER PUBLICATIONS, "Lane et al.", reference, replace "f(ab+e,acu +ee )$_2$" with -- F(ab')$_2$ --.

Drawings,
Delete Fig. 6 and replace with the attached Fig. 6.

Column 32,
Line 23, after "through 7" insert -- of --.

Signed and Sealed this

Thirteenth Day of January, 2004

JON W. DUDAS
*Acting Director of the United States Patent and Trademark Office*

SEQUENCE LISTING

<160> NUMBER OF SEQ ID NOS: 14

<210> SEQ ID NO 1
<211> LENGTH: 2292
<212> TYPE: DNA
<213> ORGANISM: Homo sapiens
<220> FEATURE:
<221> NAME/KEY: CDS
<222> LOCATION: (1)...(2292)

<400> SEQUENCE: 1

```
atg gag agc aag gtg ctg ctg gcc gtc gcc ctg tgg ctc tgc gtg gag      48
Met Glu Ser Lys Val Leu Leu Ala Val Ala Leu Trp Leu Cys Val Glu
 1               5                  10                  15
```

-continued

```
acc cgg gcc gcc tct gtg ggt ttg cct agt gtt tct ctt gat ctg ccc       96
Thr Arg Ala Ala Ser Val Gly Leu Pro Ser Val Ser Leu Asp Leu Pro
            20                  25                  30 agg ctc agc ata caa aaa gac ata ctt aca att aag gct aat aca act      144
Arg Leu Ser Ile Gln Lys Asp Ile Leu Thr Ile Lys Ala Asn Thr Thr
        35                  40                  45 ctt caa att act tgc agg gga cag agg gac ttg gac tgg ctt tgg ccc      192
Leu Gln Ile Thr Cys Arg Gly Gln Arg Asp Leu Asp Trp Leu Trp Pro
50                  55                  60 aat aat cag agt ggc agt gag caa agg gtg gag gtg act gag tgc agc      240
Asn Asn Gln Ser Gly Ser Glu Gln Arg Val Glu Val Thr Glu Cys Ser
65                  70                  75                  80 gat ggc ctc ttc tgt aag aca ctc aca att cca aaa gtg atc gga aat      288
Asp Gly Leu Phe Cys Lys Thr Leu Thr Ile Pro Lys Val Ile Gly Asn
            85                  90                  95 gac act gga gcc tac aag tgc ttc tac cgg gaa act gac ttg gcc tcg      336
Asp Thr Gly Ala Tyr Lys Cys Phe Tyr Arg Glu Thr Asp Leu Ala Ser
            100                 105                 110 gtc att tat gtc tat gtt caa gat tac aga tct cca ttt att gct tct      384
Val Ile Tyr Val Tyr Val Gln Asp Tyr Arg Ser Pro Phe Ile Ala Ser
        115                 120                 125 gtt agt gac caa cat gga gtc gtg tac att act gag aac aaa aac aaa      432
Val Ser Asp Gln His Gly Val Val Tyr Ile Thr Glu Asn Lys Asn Lys
130                 135                 140 act gtg gtg att cca tgt ctc ggg tcc att tca aat ctc aac gtg tca      480
Thr Val Val Ile Pro Cys Leu Gly Ser Ile Ser Asn Leu Asn Val Ser
145                 150                 155                 160 ctt tgt gca aga tac cca gaa aag aga ttt gtt cct gat ggt aac aga      528
Leu Cys Ala Arg Tyr Pro Glu Lys Arg Phe Val Pro Asp Gly Asn Arg
            165                 170                 175 att tcc tgg gac agc aag aag ggc ttt act att ccc agc tac atg atc      576
Ile Ser Trp Asp Ser Lys Lys Gly Phe Thr Ile Pro Ser Tyr Met Ile
            180                 185                 190 agc tat gct ggc atg gtc ttc tgt gaa gca aaa att aat gat gaa agt      624
Ser Tyr Ala Gly Met Val Phe Cys Glu Ala Lys Ile Asn Asp Glu Ser
        195                 200                 205 tac cag tct att atg tac ata gtt gtc gtt gta ggg tat agg att tat      672
Tyr Gln Ser Ile Met Tyr Ile Val Val Val Gly Tyr Arg Ile Tyr
        210                 215                 220 gat gtg gtt ctg agt ccg tct cat gga att gaa cta tct gtt gga gaa      720
Asp Val Val Leu Ser Pro Ser His Gly Ile Glu Leu Ser Val Gly Glu
225                 230                 235                 240 aag ctt gtc tta aat tgt aca gca aga act gaa cta aat gtg ggg att      768
Lys Leu Val Leu Asn Cys Thr Ala Arg Thr Glu Leu Asn Val Gly Ile
            245                 250                 255 gac ttc aac tgg gaa tac cct tct tcg aag cat cag cat aag aaa ctt      816
Asp Phe Asn Trp Glu Tyr Pro Ser Ser Lys His Gln His Lys Lys Leu
            260                 265                 270 gta aac cga gac cta aaa acc cag tct ggg agt gag atg aag aaa ttt      864
Val Asn Arg Asp Leu Lys Thr Gln Ser Gly Ser Glu Met Lys Lys Phe
        275                 280                 285 ttg agc acc tta act ata gat ggt gta acc cgg agt gac caa gga ttg      912
Leu Ser Thr Leu Thr Ile Asp Gly Val Thr Arg Ser Asp Gln Gly Leu
        290                 295                 300 tac acc tgt gca gca tcc agt ggg ctg atg acc aag aag aac agc aca      960
Tyr Thr Cys Ala Ala Ser Ser Gly Leu Met Thr Lys Lys Asn Ser Thr
305                 310                 315                 320 ttt gtc agg gtc cat gaa aaa cct ttt gtt gct ttt gga agt ggc atg     1008
Phe Val Arg Val His Glu Lys Pro Phe Val Ala Phe Gly Ser Gly Met
            325                 330                 335
```

```
gaa tct ctg gtg gaa gcc acg gtg ggg gag cgt gtc aga atc cct gcg    1056
Glu Ser Leu Val Glu Ala Thr Val Gly Glu Arg Val Arg Ile Pro Ala
            340                 345                 350 aag tac ctt ggt tac cca ccc cca gaa ata aaa tgg tat aaa aat gga    1104
Lys Tyr Leu Gly Tyr Pro Pro Pro Glu Ile Lys Trp Tyr Lys Asn Gly
            355                 360                 365 ata ccc ctt gag tcc aat cac aca att aaa gcg ggg cat gta ctg acg    1152
Ile Pro Leu Glu Ser Asn His Thr Ile Lys Ala Gly His Val Leu Thr
        370                 375                 380 att atg gaa gta agt gaa aga gac aca gga aat tac act gtc atc ctt    1200
Ile Met Glu Val Ser Glu Arg Asp Thr Gly Asn Tyr Thr Val Ile Leu
385                 390                 395                 400 acc aat ccc att tca aag gag aag cag agc cat gtg gtc tct ctg gtt    1248
Thr Asn Pro Ile Ser Lys Glu Lys Gln Ser His Val Val Ser Leu Val
            405                 410                 415 gtg tat gtc cca ccc cag att ggt gag aaa tct cta atc tct cct gtg    1296
Val Tyr Val Pro Pro Gln Ile Gly Glu Lys Ser Leu Ile Ser Pro Val
            420                 425                 430 gat tcc tac cag tac ggc acc act caa acg ctg aca tgt acg gtc tat    1344
Asp Ser Tyr Gln Tyr Gly Thr Thr Gln Thr Leu Thr Cys Thr Val Tyr
            435                 440                 445 gcc att cct ccc ccg cat cac atc cac tgg tat tgg cag ttg gag gaa    1392
Ala Ile Pro Pro Pro His His Ile His Trp Tyr Trp Gln Leu Glu Glu
450                 455                 460 gag tgc gcc aac gag ccc agc caa gct gtc tca gtg aca aac cca tac    1440
Glu Cys Ala Asn Glu Pro Ser Gln Ala Val Ser Val Thr Asn Pro Tyr
465                 470                 475                 480 cct tgt gaa gaa tgg aga agt gtg gag gac ttc cag gga gga aat aaa    1488
Pro Cys Glu Glu Trp Arg Ser Val Glu Asp Phe Gln Gly Gly Asn Lys
            485                 490                 495 att gaa gtt aat aaa aat caa ttt gct cta att gaa gga aaa aac aaa    1536
Ile Glu Val Asn Lys Asn Gln Phe Ala Leu Ile Glu Gly Lys Asn Lys
            500                 505                 510 act gta agt acc ctt gtt atc caa gcg gca aat gtg tca gct ttg tac    1584
Thr Val Ser Thr Leu Val Ile Gln Ala Ala Asn Val Ser Ala Leu Tyr
            515                 520                 525 aaa tgt gaa gcg gtc aac aaa gtc ggg aga gga gag agg gtg atc tcc    1632
Lys Cys Glu Ala Val Asn Lys Val Gly Arg Gly Glu Arg Val Ile Ser
530                 535                 540 ttc cac gtg acc agg ggt cct gaa att act ttg caa cct gac atg cag    1680
Phe His Val Thr Arg Gly Pro Glu Ile Thr Leu Gln Pro Asp Met Gln
545                 550                 555                 560 ccc act gag cag gag agc gtg tct ttg tgg tgc act gca gac aga tct    1728
Pro Thr Glu Gln Glu Ser Val Ser Leu Trp Cys Thr Ala Asp Arg Ser
            565                 570                 575 acg ttt gag aac ctc aca tgg tac aag ctt ggc cca cag cct ctg cca    1776
Thr Phe Glu Asn Leu Thr Trp Tyr Lys Leu Gly Pro Gln Pro Leu Pro
            580                 585                 590 atc cat gtg gga gag ttg ccc aca cct gtt tgc aag aac ttg gat act    1824
Ile His Val Gly Glu Leu Pro Thr Pro Val Cys Lys Asn Leu Asp Thr
            595                 600                 605 ctt tgg aaa ttg aat gcc acc atg ttc tct aat agc aca aat gac att    1872
Leu Trp Lys Leu Asn Ala Thr Met Phe Ser Asn Ser Thr Asn Asp Ile
            610                 615                 620 ttg atc atg gag ctt aag aat gca tcc ttg cag gac caa gga gac tat    1920
Leu Ile Met Glu Leu Lys Asn Ala Ser Leu Gln Asp Gln Gly Asp Tyr
625                 630                 635                 640 gtc tgc ctt gct caa gac agg aag acc aag aaa aga cat tgc gtg gtc    1968
Val Cys Leu Ala Gln Asp Arg Lys Thr Lys Lys Arg His Cys Val Val
```

```
                      645                 650                 655
agg cag ctc aca gtc cta gag cgt gtg gca ccc acg atc aca gga aac    2016
Arg Gln Leu Thr Val Leu Glu Arg Val Ala Pro Thr Ile Thr Gly Asn
            660                 665                 670 ctg gag aat cag acg aca agt att ggg gaa agc atc gaa gtc tca tgc    2064
Leu Glu Asn Gln Thr Thr Ser Ile Gly Glu Ser Ile Glu Val Ser Cys
            675                 680                 685 acg gca tct ggg aat ccc cct cca cag atc atg tgg ttt aaa gat aat    2112
Thr Ala Ser Gly Asn Pro Pro Pro Gln Ile Met Trp Phe Lys Asp Asn
    690                 695                 700 gag acc ctt gta gaa gac tca ggc att gta ttg aag gat ggg aac cgg    2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc    2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc    2256
Cys Gln Ala Cys Ser Val Leu Gly Cys Ala Lys Val Glu Ala Phe Phe
            740                 745                 750 ata ata gaa ggt gcc cag gaa aag acg aac ttg gaa                    2292
Ile Ile Glu Gly Ala Gln Glu Lys Thr Asn Leu Glu
            755                 760

<210> SEQ ID NO 2
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 2
atggagagca aggtgctgct g                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 3
acgctctagg actgtgagct g                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 4
agattccatg ccacttccaa a                                             21

<210> SEQ ID NO 5
<211> LENGTH: 45
<212> TYPE: DNA
<213> ORGANISM: Artificial Sequence
<220> FEATURE:
<223> OTHER INFORMATION: Synthetically generated primer

<400> SEQUENCE: 5
ttctcggatc ctataaatat ggagagcaag gtgctgctgg ccgtc                   45
```

```
<210> SEQ ID NO 6
<211> LENGTH: 53
<212> TYPE: DNA
<213> ORGANISM: Artificial Sequence
<220> FEATURE:
<223> OTHER INFORMATION: Synthetically generated primer

<400> SEQUENCE: 6
ttctcgaatt cttagtggtg gtggtggtgg tgacgctcta ggactgtgag ctg        53

<210> SEQ ID NO 7
<211> LENGTH: 50
<212> TYPE: DNA
<213> ORGANISM: Artificial Sequence
<220> FEATURE:
<223> OTHER INFORMATION: Synthetically generated primer

<400> SEQUENCE: 7
ttctcgaatt cttagtggtg gtggtggtgg tgagattcca tgccacttcc            50

<210> SEQ ID NO 8
<211> LENGTH: 42
<212> TYPE: DNA
<213> ORGANISM: Artificial Sequence
<220> FEATURE:
<223> OTHER INFORMATION: Synthetically generated primer

<400> SEQUENCE: 8
tttgtcacaa gatttgggct ccggactcag aaccacatca ta                    42

<210> SEQ ID NO 9
<211> LENGTH: 42
<212> TYPE: DNA
<213> ORGANISM: Artificial Sequence
<220> FEATURE:
<223> OTHER INFORMATION: Synthetically generated primer

<400> SEQUENCE: 9
tttgtcacaa gatttgggct cagattccat gccacttcca aa                    42

<210> SEQ ID NO 10
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 10
tcttgtgaca aaactcacac atgc                                        24

<210> SEQ ID NO 11
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 11
cggagacagg gagaggctct tctg                                        24

<210> SEQ ID NO 12
<211> LENGTH: 21
<212> TYPE: DNA
<213> ORGANISM: Artificial Sequence
<220> FEATURE:
<223> OTHER INFORMATION: Synthetically generated primer
```

-continued

```
<400> SEQUENCE: 12
gagcccaaat cttgagacaa a                                              21

<210> SEQ ID NO 13
<211> LENGTH: 49
<212> TYPE: DNA
<213> ORGANISM: Artificial Sequence
<220> FEATURE:
<223> OTHER INFORMATION: Synthetically generated primer

<400> SEQUENCE: 13
ttcttctaga ttagtggtgg tggtggtggt gtttacccgg agacaggga               49

<210> SEQ ID NO 14
<211> LENGTH: 764
<212> TYPE: PRT
<213> ORGANISM: Homo sapiens

<400> SEQUENCE: 14
```

Met Glu Ser Lys Val Leu Leu Ala Val Ala Leu Trp Leu Cys Val Glu
 1               5                  10                  15

Thr Arg Ala Ala Ser Val Gly Leu Pro Ser Val Ser Leu Asp Leu Pro
             20                  25                  30

Arg Leu Ser Ile Gln Lys Asp Ile Leu Thr Ile Lys Ala Asn Thr Thr
         35                  40                  45

Leu Gln Ile Thr Cys Arg Gly Gln Arg Asp Leu Asp Trp Leu Trp Pro
     50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
                 85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu

-continued

```
            290                 295                 300
Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Glu Ile Lys Trp Tyr Lys Asn Gly
                355                 360             365

Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445

Ala Ile Pro Pro Pro His His Ile His Trp Tyr Trp Gln Leu Glu Glu
                450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
                595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
                675                 680                 685

Thr Ala Ser Gly Asn Pro Pro Pro Gln Ile Met Trp Phe Lys Asp Asn
                690                 695                 700

Glu Thr Leu Val Glu Asp Ser Gly Ile Val Leu Lys Asp Gly Asn Arg
705                 710                 715                 720
```

```
Asn Leu Thr Ile Arg Arg Val Arg Lys Glu Asp Glu Gly Leu Tyr Thr
                725             730                 735
Cys Gln Ala Cys Ser Val Leu Gly Cys Ala Lys Val Glu Ala Phe Phe
            740             745                 750
Ile Ile Glu Gly Ala Gln Glu Lys Thr Asn Leu Glu
        755             760
```